(12) United States Patent
Ishii et al.

(10) Patent No.: US 8,653,295 B2
(45) Date of Patent: Feb. 18, 2014

(54) PROCESS FOR PRODUCING α-TRIFLUOROMETHYL-α,β-UNSATURATED ESTER

(75) Inventors: Akihiro Ishii, Kawagoe (JP); Manabu Yasumoto, Kawagoe (JP); Takako Yamazaki, Kawagoe (JP); Kaori Mogi, Kawagoe (JP); Kazunori Mori, Iruma-gun (JP); Takashi Masuda, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 528 days.

(21) Appl. No.: 13/060,565

(22) PCT Filed: Sep. 24, 2009

(86) PCT No.: PCT/JP2009/066527
§ 371 (c)(1),
(2), (4) Date: Feb. 24, 2011

(87) PCT Pub. No.: WO2010/035747
PCT Pub. Date: Apr. 1, 2010

(65) Prior Publication Data
US 2011/0160477 A1   Jun. 30, 2011

(30) Foreign Application Priority Data

Sep. 26, 2008   (JP) .................. 2008-247053

(51) Int. Cl.
*C07C 69/76* (2006.01)
(52) U.S. Cl.
USPC ......................................... 560/104
(58) Field of Classification Search
None
See application file for complete search history.

(56) References Cited

U.S. PATENT DOCUMENTS

| 4,650,511 | A | 3/1987 | Koya et al. |
| 7,807,858 | B2 | 10/2010 | Ishii et al. |
| 2006/0004195 | A1* | 1/2006 | Deng et al. ............ 540/603 |

FOREIGN PATENT DOCUMENTS

| EP | 0 768 296 A1 | 4/1997 |
| JP | 60-78941 A | 5/1985 |
| JP | 2003-342211 A | 12/2003 |
| JP | 2006-290870 A | 10/2006 |
| JP | 2008-13519 A | 1/2008 |
| JP | 2008-505092 A | 2/2008 |

OTHER PUBLICATIONS

Takashi Yamazaki et al, "Stereoselective Preparation of Ethyl 2,3-Dihydroxy-4,4,4-trifluorobutyrates via Enzymatic Optical Resolution", 1990, Tetrahedrom: Asymmetry, vol. 1, No. 8, pp. 521-524, Pergamon Press plc, Great Britain.
Pat F. Bevilacqua et al., "Sulfazecin Analogues. Preparation of 4-(Trifluoromethyl)-1-sulfo-2-azetidinone Derivatives", 1984, vol. 49, No. 8, pp. 1430-1434, Journal of Organic Chemistry, USA (XP 000650171).
George A. Olah et al., "Synthetic Methods and Reactions; 83. Sulfuryl Chloride Fluoride, a Mild Dehydrating Agent in the Preparation of Nitriles from Aldoximes", 1980, No. 8., p. 659, Georg Thieme Verlag, Germany and New York, USA.
Scott A. Kinkead et al., "Reactions of Polyfluoroalkyl Fluorosulfates with Nucleophiles: An Unuaual Substitution at the Sulfur-Fluorine Bond", 1984, Journal of the American Chemical Society, vol. 106, No. 24, pp. 7496-7500, ACS Publications, USA (XP008149269).
L.A. Motnyak et al., "Reaction of Hydroxy and Carbonyl Compounds with Sulphur Tetrafluoride. XII. Reactions of Ester of Aliphatic α- and β-Hydroxy Carboxylic Acids with Sulphur Tetrafluoride", 1984, Journal of Organic Chemistry of the USSR, vol. 20, No. 6, pp. 1063-1074, Plenum Publishing Corp. (XP 000650130).
Supplementary European Search Report dated Jul. 25, 2013 (Seven (7) pages).
Mendeleev Communications (Russia), 2006, pp. 175-177.
Izvestiya Akademi Nauk, Seriya Khimicheskaya (Russia), 1992, pp. 2617-2623.
Journal of Fluorine Chemistry (Netherlands), 1991, vol. 51, pp. 323-334.
Zhurnal Organicheskoi Khimii (Russia), 1989, vol. 25, pp. 2523-2527.
Journal of Fluorine Chemistry (Netherlands), 1982, vol. 21, pp. 377-384.
Journal of the Chemical Society (U.K.), 1961, pp. 4519-4521.
"Protective Groups in Organic Synthesis", Third Edition, 1999, John Wiley & Sons, Inc.
Tetrahedron, 2002, vol. 58, pp. 8565-8571.
Tetrahedron Letters (U.K.), 2004, vol. 45, pp. 183-185.
International Search Report including English translation dated Nvember 24, 2009 and PCT/ISA/237 Form (Eight (8) pages).

* cited by examiner

*Primary Examiner* — Johann R Richter
*Assistant Examiner* — Jennifer C Sawyer
(74) *Attorney, Agent, or Firm* — Crowell & Moring LLP

(57) ABSTRACT

An α-trifluoromethyl-α,β-unsaturated ester can be produced by reacting an α-trifluoromethyl-α-hydroxy ester with sulfuryl fluoride ($SO_2F_2$) in the presence of an organic base. It is preferable that the raw substrate has a hydrogen atom as one β-position substituent group and either an alkyl group, a substituted alkyl group, an alkenyl group, a substituted alkenyl group, an aromatic ring group or a substituted aromatic ring group as the other β-position substituent group. It is more preferable that an ester moiety of the raw substrate is an alkyl ester. This raw substrate is readily available. Further, the desired reaction can proceed favorably with the use of this raw substrate. It is also preferable to use either 1,5-diazabicyclo[4.3.0]non-5-ene (DBN) or 1,8-diazabicyclo[5.4.0]undec-7-ene (DBU) as the organic base. The desired reaction can proceed more favorably with the use of this organic base.

3 Claims, No Drawings

PROCESS FOR PRODUCING α-TRIFLUOROMETHYL-α,β-UNSATURATED ESTER

TECHNICAL FIELD

The present invention relates to a process for producing α-trifluoromethyl-α,β-unsaturated esters, which are important as intermediates for pharmaceutical and agricultural chemicals.

BACKGROUND ART

It is known that α-trifluoromethyl-α,β-unsaturated esters are important as intermediates for pharmaceutical and agricultural chemicals. There have been reported, as conventional production techniques relevant to the present invention, dehydration processes that use thionyl chloride ($SOCl_2$), diphosphorus pentaoxide ($P_2O_5$), acetic anhydride $[(CH_3CO)_2O]$ and trifluoromethanesulfonic acid anhydride $[(CF_3SO_2)_2O]$ as dehydrating agents (see Non-Patent Documents 1 to 6 and Patent Document 1). Among others, the process using the trifluoromethanesulfonic acid anhydride is applicable to even raw substrates in which the acidity of the β-position proton is low (whereby the desired reaction is unlikely to proceed) and is thus regarded as one most superior process.

Further, the present applicant has disclosed a process of dehydroxyfluorination of an alcohol with the combined use of sulfuryl fluoride ($SO_2F_2$) and an organic base (see Patent Document 2).

PRIOR ART DOCUMENTS

Patent Documents

Patent Document 1: U.S. Patent Application Publication No. 2006/0004195
Patent Document 2: Japanese Laid-Open Patent Publication No. 2006-290870

Non-Patent Documents

Non-Patent Document 1: Mendeleev Communications (Russia), 2006, P. 175-177.
Non-Patent Document 2: Izvestiya Akademi Nauk, Seriya Khimicheskaya (Russia), 1992, P. 2617-2623
Non-Patent Document 3: Journal of Fluorine Chemistry (Netherlands), 1991, Vol. 51, P. 323-334
Non-Patent Document 4: Zhurnal Organicheskoi Khimii (Russia), 1989, Vol. 25, P. 2523-2527
Non-Patent Document 5: Journal of Fluorine Chemistry (Netherlands), 1982, Vol. 21, P. 377-384
Non-Patent Document 6: Journal of the Chemical Society (U.K.), 1961, P. 4519-4521

DISCLOSURE OF THE INVENTION

It is an object of the present invention to provide a practical production process of an α-trifluoromethyl-α,β-unsaturated ester. In order to achieve the object of the present invention, it is necessary to solve problems in the prior art techniques.

The processes of Non-Patent Documents 1 to 6 are limited to applications where: the β-proton of the raw substrate is high in acidity due to the presence of a neighboring electron attracting group; and a leaving group of the reaction intermediate (derived from a hydroxyl group of the raw substrate) can be readily eliminated by the electron pushing effect of the conjugated system. The applicable substrate ranges of the processes of Non-Patent Documents 1 to 6 are very narrow.

On the other hand, it is said that the process of Patent Document 1 has a wide applicable substrate range. There is however no disclosure in Patent Document 1 about the specific reaction conditions and yield in the case of using α-trifluoromethyl-α-hydroxyesters as raw substrates as in the case of the present invention. (It is merely stated in this patent document that the reaction is performed under conditions similar to those specified for typical reaction schemes.) Follow-up experiment has hence been conducted on the dehydration of the target substrate of the present invention, α-trifluoromethyl-α-hydroxyesters, under the suitable reaction conditions of Patent Document 1 (dehydrating agent: trifluoromethanesulfonic acid anhydride, base: pyridine, reaction solvent: methylene chloride, temperature range: 0 to 35° C.). The results of the follow-up experiment however show that the yield of the reaction is very low (see the after-mentioned Comparative Example 1 of TABLE 1 and Comparative Example 4 of TABLE 2). The cause for such a low yield is a very slow rate of elimination from the reaction intermediate to the target product (see Scheme 1). Thus, it can hardly be said that the process of Patent Document 1 is practical for production of α-trifluoromethyl-α,β-unsaturated esters.

Scheme 1

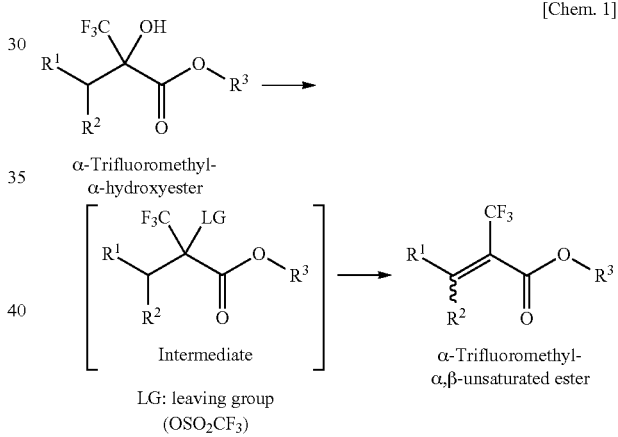

Further, although the trifluoromethanesulfonic acid anhydride has two trifluoromethanesulfonyl ($CF_3SO_2$) groups, only one of these trifluoromethanesulfonyl groups is used for conversion to the leaving group of the reaction intermediate. It cannot be thus said that trifluoromethanesulfonic acid anhydride is a preferred dehydrating agent in view of the atom economy etc. It cannot also be said that the process using the trifluoromethanesulfonic acid anhydride is suitable for large-scale production of the target product as there occur as a by-product two molecules of trifluoromethanesulfonic acid ($CF_3SO_3H$), which is difficult to decompose and causes a problem in waste treatment, per 1 molecule of the target compound.

As mentioned above, there has been a demand for a practical production process applicable to a wide range of substrate materials and capable of producing an α-trifluoromethyl-α,β-unsaturated ester with high yield in a short time (i.e. with high productivity) and with high reactant atom economy but without causing a problem in waste treatment.

The present inventors have made extensive researches in view of the above problems and, as a result, have found that it is possible to produce an α-trifluoromethyl-α,β-unsaturated ester by reacting an α-trifluoromethyl-α-hydroxy ester with sulfuryl fluoride in the presence of an organic base. The present inventors have also found that it is preferable that the α-trifluoromethyl-α-hydroxy ester used as the raw substrate has a hydrogen atom as one β-position substituent group and either an alkyl group, a substituted alkyl group, an alkenyl group, a substituted alkenyl group, an aromatic ring group or a substituted aromatic ring group as the other β-position substituent group and is more preferable that an ester moiety of the α-trifluoromethyl-α-hydroxy ester is an alkyl ester. The above raw substrate is readily available. Further, the use of the above raw substrate is advantageous in that: the desired reaction proceeds favorably; and the resulting α-trifluoromethyl-α,β-unsaturated ester is particularly important as a pharmaceutical and agricultural intermediate. The present inventors have further found that it is preferable to use either 1,5-diazabicyclo[4.3.0]non-5-ene (DBN) or 1,8-diazabicyclo[5.4.0]undec-7-ene (DBU) as the organic base. The use of the above organic base is advantageous in that the desired reaction proceeds more favorably.

The reaction conditions of the present invention are similar to the dehydroxyfluorination conditions of Patent Document 2. In fact, there could occur a fluoride by-product by replacement of an α-position hydroxyl group of the raw substrate with a fluorine atom (see Scheme-1; Example 1). It has however been shown that the α-trifluoromethyl-α,β-unsaturated ester can be obtained selectively as the dehydration product by the use of the α-trifluoromethyl-α-hydroxy ester as the raw substrate in the present invention.

Scheme-1 (Example 1)

[Chem. 2]

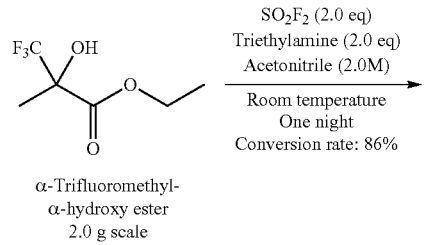

α-Trifluoromethyl-
α-hydroxy ester
2.0 g scale

SO$_2$F$_2$ (2.0 eq)
Triethylamine (2.0 eq)
Acetonitrile (2.0M)

Room temperature
One night
Conversion rate: 86%

-continued

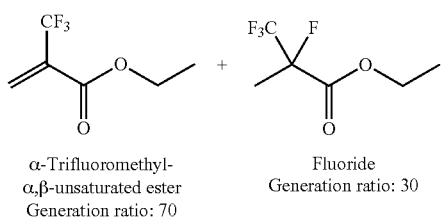

α-Trifluoromethyl-
α,β-unsaturated ester
Generation ratio: 70

Fluoride
Generation ratio: 30

It has also been shown that, although trifluoromethanesulfonyl fluoride (CF$_3$SO$_2$F) and sulfuryl fluoride are expected to have the same effects as the reactant, the use of sulfuryl fluoride leads to a far superior conversion rate and GC purity to those by the use of trifluoromethanesulfonyl fluoride (see comparisons of Example 2 and Comparative Example 2 and of Example 3 and Comparative Example 3 in TABLE 1).

It has further been shown that, although the desired reaction proceeds favorably even with the use of triethylamine as the organic base, the use of 1,8-diazabicyclo[5.4.0]undec-7-ene leads to a superior GG purity to that by the use of triethylamine (see comparison of Examples 2 and 3 in TABLE 1 and comparison of Examples 4 and 5 in TABLE 2); and it is particularly preferable to use the organic base stronger in basicity than triethylamine (more specifically, not only 1,8-diazabicyclo[5.4.0]undec-7-ene, but also 4-dimethylaminopyridine (DMAP), 1,5-diazabicyclo[4.3.0]non-5-ene (DBN), N,N,N',N',N''-pentamethylguanidine, 1,5,7-triazabicyclo[4.4.0]dec-5-ene (TBD), or phosphazene base such as BEMP or t-Bu—P4).

TABLE 1

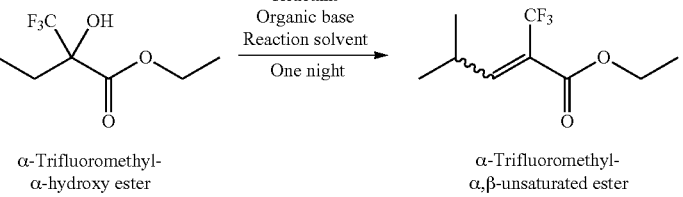

α-Trifluoromethyl-
α-hydroxy ester

Reactant
Organic base
Reaction solvent
One night

α-Trifluoromethyl-
α,β-unsaturated ester

| | Scale | Reactant | Organic base | Reaction solvent | Temperature condition | Conversion rate | GC purity[a] |
|---|---|---|---|---|---|---|---|
| Comparative Example 1 | 0.3 g | (CF$_3$SO$_2$)$_2$O (1.6 eq) | pyridine (2.5 eq) | methylene chloride (0.3 M) | room temperature | 86% | 0.7% (60:40) |
| Comparative Example 2 | 2.0 g | CF$_3$SO$_2$F (2.0 eq) | triethyl amine (3.0 eq) | acetonitrile (1.0 M) | room temperature | 31% | 9.1% (30:70) |
| Comparative Example 3 | 1.0 g | CF$_3$SO$_2$F (2.0 eq) | DBU[b] (3.0 eq) | acetonitrile (0.9 M) | 50° C. | 100% | 32.2% (79:21) |

TABLE 1-continued

Reactant: α-Trifluoromethyl-α-hydroxy ester → α-Trifluoromethyl-α,β-unsaturated ester (Reactant / Organic base / Reaction solvent / One night)

| | Scale | Reactant | Organic base | Reaction solvent | Temperature condition | Conversion rate | GC purity[a] |
|---|---|---|---|---|---|---|---|
| Example 2 | 1.0 g | SO$_2$F$_2$ (2.0 eq) | triethyl amine (2.9 eq) | acetonitrile (0.9 M) | room temperature | 92% | 80.7%[c] (40:60) |
| Example 3 | 1.0 g | SO$_2$F$_2$ (2.0 eq) | DBU[b] (3.0 eq) | acetonitrile (0.9 M) | 50° C. | 100% | 96.9%[a] (37:63) |

[a]Gas chromatographic purity at the time of determination of conversion rate. The term inside parentheses: E:Z isomer ratio.
[b]1,8-Diazabicyclo[5.4.0]undec-7-ene.
[c]Fluoride < 5%.

TABLE 2

Reactant: α-Trifluoromethyl-α-hydroxy ester → α-Trifluoromethyl-α,β-unsaturated ester (Reactant / Organic base / Reaction solvent / One night)

| | Scale | Reactant | Organic base | Reaction solvent | Temperature condition | Conversion rate | GC purity[a] |
|---|---|---|---|---|---|---|---|
| Comparative Example 4 | 1.0 g | (CF$_3$SO$_2$)$_2$O (2.0 eq) | pyridine (5.0 eq) | methylene chloride (0.2 M) | room temperature | 53% | 2.6% (E isomer[b]) |
| Example 4 | 2.0 g | SO$_2$F$_2$ (2.0 eq) | DBU[c] (3.0 eq) | acetonitrile (0.8 M) | 50° C. | 95% | 90.6%[d] (90:10) |
| Example 5 | 1.0 g | SO$_2$F$_2$ (2.0 eq) | triethyl amine (2.0 eq) DBU[c] (0.5 eq) | acetonitrile (0.8 M) | 50° C. | 95% | 80.2%[d] (90:10) |

[a]Gas chromatographic purity at the time of determination of conversion rate.
[b]Z isomer in a trace amount.
[c]1,8-Diazabicyclo[5.4.0]undec-7-ene.
[d]Fluoride < 5%.

In this way, the present inventors have found the particularly useful techniques for production of the α-trifluoromethyl-α,β-unsaturated ester. The present invention is based on these findings.

Namely, the present invention provides a practical process for producing an α-trifluoromethyl-α,β-unsaturated ester as defined as follows by Inventive Aspects 1 to 3.

[Inventive Aspect 1]

A process for producing an α-trifluoromethyl-α,β-unsaturated ester of the general formula [2], comprising: reacting an α-trifluoromethyl-α-hydroxy ester of the general formula [1] with sulfuryl fluoride (SO$_2$F$_2$) in the presence of an organic base

[Chem. 3]

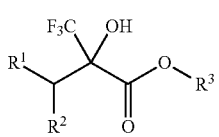

[1]

-continued

[Chem. 4]

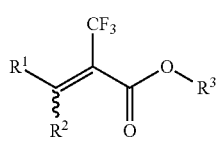
[2]

where $R^1$ and $R^2$ each independently represent a hydrogen atom, an alkyl group, a substituted alkyl group, an alkenyl group, a substituted alkenyl group, an alkynyl group, a substituted alkynyl group, an aromatic ring group, a substituted aromatic ring group, an alkylcarbonyl group, a substituted alkylcarbonyl group, an alkoxycarbonyl group, a substituted alkoxycarbonyl group, an arylcarbonyl group, a substituted arylcarbonyl group, a cyano group or a nitro group; $R^3$ represents an alkyl group or a substituted alkyl group; and the wavy line in the general formula (2) indicates that the double bond is in an E-isomer configuration, a Z-isomer configuration or a mixture thereof.

[Inventive Aspect 2]

A process for producing an α-trifluoromethyl-α,β-unsaturated ester of the general formula [4], comprising: reacting an α-trifluoromethyl-α-hydroxy ester of the general formula [3] with sulfuryl fluoride ($SO_2F_2$) in the presence of an organic base

[Chem. 5]

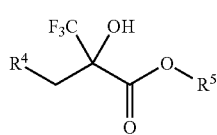
[3]

[Chem. 6]

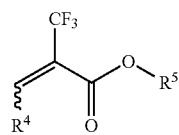
[4]

where $R^4$ represents an alkyl group, a substituted alkyl group, an alkenyl group, a substituted alkenyl group, an aromatic ring group or a substituted aromatic ring group; $R^5$ represents an alkyl group; the wavy line in the general formula [4] indicates that the double bond is in an E-isomer configuration, a Z-isomer configuration or a mixture thereof.

[Inventive Aspect 3]

The process for producing the α-trifluoromethyl-α,β-unsaturated ester according to Inventive Aspect 1 or 2, wherein the organic base is either 1,5-diazabicyclo[4.3.0]non-5-ene (DBN) or 1,8-diazabicyclo[5.4.0]undec-7-ene (DBU).

DETAILED DESCRIPTION

The advantages of the present invention over the prior art techniques will be explained below.

The production process of the present invention is applicable to a wide range of substrate materials. Further, it is possible by the production process of the present invention that the target compound can be obtained with high productivity and high yield. It is also possible that the target compound can be obtained with high chemical purity as there occurs almost no difficult-to-separate by-product. The sulfuryl fluoride used in the present invention has high atom economy and can be easily processed into inorganic salts e.g. fluorite ($CaF_2$) and calcium sulfate ($CaSO_4$) that do not raise particular problems. In addition, the sulfuryl fluoride is widely used as a fumigant and available in a large quantity at low cost as compared to the other dehydrating agents such as trifluoromethanesulfonic acid anhydride and fluorosulfuric acid anhydride (($FSO_2$)$_2$O) as disclosed in Patent Document 1.

As mentioned above, the production process of the present invention solves all of the prior art problems and can be applied for industrial uses. So far as the present inventors know, there has been no report about organic synthesis example using, as a dehydrating agent, sulfuryl fluoride that is widely known and used as the fumigant.

The production process of the α-trifluoromethyl-α,β-unsaturated ester according to the present invention will be described in detail below.

According to the present invention, an α-trifluoromethyl-α,β-unsaturated ester of the general formula [2] is produced by reaction of an α-trifluoromethyl-α-hydroxy ester of the general formula [1] with sulfuryl fluoride in the presence of an organic base.

In the α-trifluoromethyl-α-hydroxy ester of the general formula [1], $R^1$ and $R^2$ each independently represents a hydrogen atom, an alkyl group, a substituted alkyl group, an alkenyl group, a substituted alkenyl group, an alkynyl group, a substituted alkynyl group, an aromatic ring group, a substituted aromatic ring group, an alkylcarbonyl group, a substituted alkylcarbonyl group, an alkoxycarbonyl group, a substituted alkoxycarbonyl group, an arylcarbonyl group, a substituted arylcarbonyl group, a cyano group or a nitro group. Among others, a hydrogen atom, an alkyl group, a substituted alkyl group, an alkenyl group, a substituted alkenyl group, an aromatic ring group and a substituted aromatic ring group are preferred as $R^1$ and $R^2$. It is more preferred that one of $R^1$ and $R^2$ is a hydrogen atom and the other of $R^1$ and $R^2$ is either an alkyl group, a substituted alkyl group, an alkenyl group, a substituted alkenyl group, an aromatic ring group or a substituted aromatic ring group.

Herein, the alkyl group generally has 1 to 18 carbon atoms and can be in the form of a linear or branched structure, or a cyclic structure (in the case of 3 or more carbon atoms). The alkenyl group refers to that in which any number of single bonds between any two adjacent carbon atoms of the above alkyl group has been replaced with a double bond. In this case, the double bond can be in an E-isomer configuration, a Z-isomer configuration or a mixture thereof. The alkynyl group refers to that in which any number of single bonds between any two adjacent carbon atoms of the above alkyl group has been replaced with a triple bond. The aromatic ring group generally has 1 to 18 carbon atoms and can be an aromatic hydrocarbon group such as phenyl, naphthyl or anthryl, or an aromatic heterocyclic group containing a hetero atom e.g. a nitrogen atom, an oxygen atom or a sulfur atom, such as pyrrolyl, furyl, thienyl, indolyl, benzofuryl or benzothienyl. The alkyl moiety (R) of the alkylcarbonyl group (—COR) is the same as the above alkyl group. The alkyl moiety (R) of the alkoxycarbonyl group (—$CO_2R$) is also the same as the above alkyl group. The aryl moiety (Ar) of the arylcarbonyl group (—COAr) is the same as the above aromatic ring group.

Any of the carbon atoms of the alkyl group, the alkenyl group, the alkynyl group, the aromatic ring group, the alkylcarbonyl group, the alkoxycarbonyl group and the arylcarbonyl group may be replaced with any number of and any combination of substituents (which correspond to the substituted alkyl group, the substituted alkenyl group, the substituted alkynyl group, the substituted aromatic ring group, the substituted alkylcarbonyl group, the substituted alkoxycarbonyl group and the substituted arylcarbonyl group, respectively). Examples of such substituents are: halogen atoms such as fluorine, chlorine, bromine and iodine; azide group; nitro group; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; lower alkylamino groups such as dimethylamino, diethylamino and dipropylamino; lower alkylthio groups such as methylthio, ethylthio and propylthio; cyano group; lower alkoxycarbonyl groups such as methoxycarbonyl, ethoxycarbonyl and propoxycarbonyl; aminocarbonyl ($CONH_2$); lower alkylaminocarbonyl groups such as dimethylaminocarbonyl, diethylaminocarbonyl and dipropylaminocarbonyl; unsaturated groups such as alkenyl groups and alkynyl groups; aromatic ring groups such as phenyl, naphthyl, pyrrolyl, furyl and thienyl; aromatic ring oxy groups such as phenoxy, naphthoxy, pyrrolyloxy, furyloxy and thienyloxy; aliphatic heterocyclic groups such as piperidyl, piperidino and morpholinyl; hydroxyl group; protected hydroxyl groups; amino group (including amino acids and peptide residues); protected amino groups; thiol group; protected thiol groups; aldehyde group; protected aldehyde groups; carboxyl group; and protected carboxyl groups.

The following terms are herein defined by the following meanings in the present specification. The term "lower" means that the group to which the term is attached has 1 to 6 carbon atoms in the form of a linear structure, a branched structure or a cyclic structure (in the case of 3 carbons or more). It means that, when the "unsaturated group" is a double bond (alkenyl group), the double bond can be in an E-isomer configuration, a Z-isomer configuration or a mixture thereof. It means that the "protected hydroxyl, amino, thiol, aldehyde and carboxyl groups" may be those having protecting groups as described in "Protective Groups in Organic Synthesis", Third Edition, 1999, John Wiley & Sons, Inc. (In this case, two or more functional groups may be protected with one protecting group.) Further, the "unsaturated group", "aromatic ring group", "aromatic ring oxy group" and "aliphatic heterocyclic group" may be substituted with halogen atoms, azide group, nitro group, lower alkyl groups, lower haloalkyl groups, lower alkoxy groups, lower haloalkoxy groups, lower alkylamino groups, lower alkylthio groups, cyano group, lower alkoxycarbonyl groups, aminocarbonyl group, lower aminocarbonyl groups, hydroxyl group, protected hydroxyl groups, amino group, protected amino groups, thiol group, protected thiol groups, aldehyde group, protected aldehyde groups, carboxyl group or protected carboxyl groups. Although some of these substituent groups could react with sulfuryl fluoride in the presence of the organic base, the desired reaction can be promoted favorably by adoption of the suitable reaction conditions.

In the α-trifluoromethyl-α-hydroxy ester of the general formula [1], $R^3$ represents an alkyl group or a substituted alkyl group. Among others, an alkyl group is preferred as $R^3$. Particularly preferred as $R^3$ is a lower alkyl group.

Examples of the alkyl group and substituted alkyl group usable as $R^3$ are the same as those mentioned above as $R^1$ and $R^2$.

The α-trifluoromethyl-α-hydroxy ester of the general formula [1] can be prepared with reference to, for example, Tetrahedron (U.K.), 2002, Vol. 58, P. 8565-8571 or Tetrahedron Letters (U.K.), 2004, Vol. 45, P. 183-185.

It suffices to use the sulfuryl fluoride in an amount of 0.7 mol or more per 1 mol of the α-trifluoromethyl-α-hydroxy ester of the general formula [1]. The amount of the sulfuryl fluoride used is generally preferably 0.8 to 10 mol, more preferably 0.9 to 5 mol, per 1 mol of the α-trifluoromethyl-α-hydroxy ester of the general formula [1].

Examples of the organic base are triethylamine, diisopropylethylamine, tri-n-propylamine, tri-n-butylamine, tri-n-pentylamine, pyridine, 2,3-lutidine, 2,4-lutidine, 2,6-lutidine, 3,4-lutidine, 3,5-lutidine, 2,4,6-collidine, 3,5,6-collidine, 4-dimethylaminopyridine, 1,5-diazabicyclo[4.3.0]non-5-ene, 1,8-diazabicyclo[5.4.0]undec-7-ene, N,N,N',N', N"-pentamethylguanidine, 1,5,7-triazabicyclo[4.4.0]dec-5-ene, and phosphazene bases such as BEMP and t-Bu—P4. Among others, triethylamine, diisopropylethylamine, tri-n-butylamine, pyridine, 2,6-lutidine, 2,4,6-collidine, 4-dimethylaminopyridine, 1,5-diazabicyclo[4.3.0]non-5-ene and 1,8-diazabicyclo[5.4.0]undec-7-ene are preferred as the organic base. Particularly preferred as the organic base are triethylamine, diisopropylethylamine, 1,5-diazabicyclo[4.3.0]non-5-ene and 1,8-diazabicyclo[5.4.0]undec-7-ene. The above organic bases can be used solely or in combination thereof.

It suffices to use the organic base in an amount of 0.7 mol or more per 1 mol of the α-trifluoromethyl-α-hydroxy ester of the general formula [1]. The amount of the organic base used is generally preferably 0.8 to 10 mol, more preferably 0.9 to 5 mol, per 1 mol of the α-trifluoromethyl-α-hydroxy ester of the general formula [1]. In the case of using two or more kinds of organic base materials in combination, the amount of the organic base used refers to the total amount of the organic base materials. Either one of the organic base materials stronger in basicity may be used in a catalytic amount (see Examples 5 to 7).

Examples of the reaction solvent are: aliphatic hydrocarbon solvents such as n-hexane, cyclohexane and n-heptane; aromatic hydrocarbon solvents such as benzene, toluene and xylene; halogenated hydrocarbon solvents such as methylene chloride, chloroform and 1,2-dichloroethane; ether solvents such as diethyl ether, tetrahydrofuran, diisopropyl ether and tert-butyl methyl ether; ester solvents such as ethyl acetate and n-butyl acetate; nitrile solvents such as acetonitrile and propionitrile; amide solvents such as N,N-dimethylformamide, N,N-dimethylacetoamide and 1,3-dimethyl-2-imidazolidinone; and dimethyl sulfoxide. Among others, n-hexane, n-heptane, toluene, xylene, methylene chloride, tetrahydrofuran, diisopropyl ether, tert-butyl methyl ether, ethyl acetate, acetonitrile, propionitrile, N,N-dimethylformamide and dimethyl sulfoxide are preferred as the reaction solvent. Particularly preferred as the reaction solvent are n-heptane, toluene, methylene chloride, tetrahydrofuran, tert-butyl methyl ether, ethyl acetate, acetonitrile and N,N-dimethylformamide. The above reaction solvents can be used solely or in combination thereof. In the present invention, the reaction may alternatively be conducted in the absence of the reaction solvent.

It suffices to use the reaction solvent in an amount of 0.01 L (liter) or more per 1 mol of the α-trifluoromethyl-α-hydroxy ester of the general formula [1]. The amount of the reaction solvent used is generally preferably 0.03 to 30 L, more preferably 0.05 to 20 L, per 1 mol of the α-trifluoromethyl-α-hydroxy ester of the general formula [1].

It suffices that the reaction temperature is in the range of −30 to +150° C. The reaction temperature is generally preferably −20 to +140° C., more preferably −10 to +130° C.

Further, it suffices that the reaction time is 24 hours or less. As the reaction time depends on the raw substrate and the reaction conditions, it is preferable to determine the time at which the raw substrate has almost disappeared as the end of the reaction while monitoring the progress of the reaction by any analytical means such as gas chromatography, liquid chromatography or nuclear magnetic resonance.

The α-trifluoromethyl-α,β-unsaturated ester of the general formula [2] can be obtained as a crude product by post treatment of the reaction terminated liquid. As one example of post treatment operation, it is feasible to dilute the reaction terminated liquid (if necessary, after concentrating the reaction terminated liquid by evaporation of the reaction solvent) with an organic solvent (such as n-hexane, n-heptane, toluene, xylene, methylene chloride, diisopropyl ether, tert-butyl methyl ether or ethyl acetate), wash the diluted liquid with water or an aqueous solution of an alkali metal inorganic base (such as sodium hydrogencarbonate, potassium hydrogencarbonate, sodium carbonate or potassium carbonate) (and, if necessary, dry the organic phase with a drying agent such as anhydrous sodium sulfate or anhydrous magnesium sulfate), and then, concentrate the recovered organic phase. The crude product can also be obtained by directly subjecting the reaction terminated liquid to distillation under reduced pressure for simplification of the post treatment operation. Further, the crude product can be purified to a high chemical purity, as needed, by purification operation such as activated carbon treatment, distillation, recrystallization or column chromatography. Herein, the wavy line in the general formula (2) indicates that the double bond of the α-trifluoromethyl-α,β-unsaturated ester is in an E-isomer configuration, a Z-isomer configuration or a mixture thereof; and the stereochemistry of the target product varies depending on the raw substrate and the reaction conditions.

As described above, the α-trifluoromethyl-α,β-unsaturated ester is produced by reaction of the α-trifluoromethyl-α-hydroxy ester with sulfuryl fluoride in the presence of the organic base (Inventive Aspect 1).

In Inventive Aspect 1, it is preferable to use the raw substrate having a hydrogen atom as one β-position substituent group and either an alkyl group, a substituted alkyl group, an alkenyl group, a substituted alkenyl group, an aromatic ring group or a substituted aromatic ring group as the other β-position substituent group and whose ester moiety is an alkyl ester (Inventive Aspect 2). This preferred raw substrate is readily available. Further, the use of this preferred raw substrate is advantageous in that: the desired reaction proceeds favorably; and the resulting α-trifluoromethyl-α,β-unsaturated ester is particularly important as a pharmaceutical and agricultural intermediate.

It is further preferable in Inventive Aspects 1 and 2 to use either 1,5-diazabicyclo[4.3.0]non-5-ene (DBN) or 1,8-diazabicyclo[5.4.0]undec-7-ene (DBU) as the organic base (Inventive Aspect 3). The desired reaction can be promoted more favorably by the use of this preferred organic base.

EXAMPLES

The present invention will be described in more detail below by way of the following examples. It should be noted that these examples are illustrative and are not intended to limit the present invention thereto.

Example 1

Into a pressure-proof reaction vessel of stainless steel (SUS) were placed 2.00 g (10.75 mmol, 1.00 eq) of α-trifluoromethyl-α-hydroxy ester of the following formula:

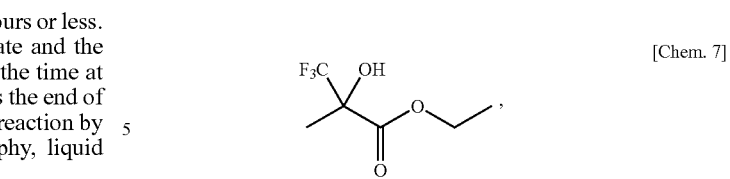

[Chem. 7]

5.4 mL (1.99 M) of acetonitrile and 2.17 g (21.44 mmol, 1.99 eq) of triethylamine. The reaction vessel was immersed in a cooling bath of −78° C., followed by blowing 2.19 g (21.46 mmol, 2.00 eq) of sulfuryl fluoride ($SO_2F_2$) from a cylinder into the reaction vessel. The resulting liquid was stirred for one night at room temperature.

It was determined by $^{19}$F-NMR of the reaction terminated liquid that the conversion rate of the reaction was 86%. It was also confirmed from the $^{19}$F-NMR results for determination of the reaction conversion rate that the generation ratio of α-trifluoromethyl-α,β-unsaturated ester of the following formula:

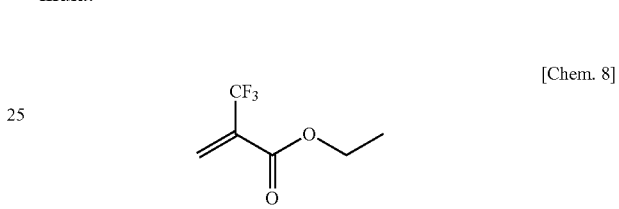

[Chem. 8]

to a fluoride of the following formula:

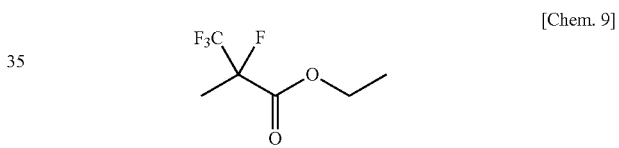

[Chem. 9]

was 70:30. No post treatment was performed on the reaction terminated liquid. The $^1$H-NMR and $^{19}$F-NMR data of the product are indicated below.

$^1$H-NMR [reference material: $(CH_3)_4Si$, deuterium solvent: $CDCl_3$] δ ppm; α-trifluoromethyl-α,β-unsaturated ester/1.35 (t, 7.1 Hz, 3H), 4.32 (q, 7.1 Hz, 2H), 6.42 (s, 1H), 6.72 (s, 1H); fluoride/1.25-1.45 (t, 3H), 2.75-3.50 (m, 3H), 4.25-4.50 (q, 2H).

$^{19}$F-NMR [reference material: $C_6F_6$, deuterium solvent: $CDCl_3$] δ ppm; α-trifluoromethyl-α,β-unsaturated ester/ 96.06 (s, 3F); fluoride/31.88 (s, 1F), 83.73 (s, 3F).

Example 2

Into a pressure-proof reaction vessel of stainless steel (SUS) were placed 1.00 g (4.38 mmol, 1.00 eq) of α-trifluoromethyl-α-hydroxy ester of the following formula:

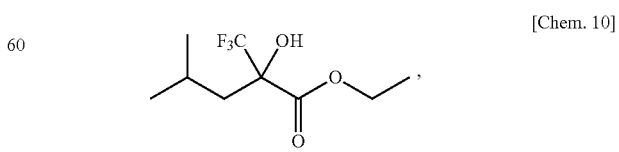

[Chem. 10]

5.0 mL (0.88 M) of acetonitrile and 1.30 g (12.85 mmol, 2.93 eq) of triethylamine. The reaction vessel was immersed in a cooling bath of −78° C., followed by blowing 0.89 g (8.72 mmol, 1.99 eq) of sulfuryl fluoride (SO₂F₂) from a cylinder into the reaction vessel. The resulting liquid was stirred for one night at room temperature.

It was determined by gas chromatography of the reaction terminated liquid that the conversion rate of the reaction was 92%. It was also confirmed that the reaction product had a gas chromatographic purity of 80.7% (intermediate [LG; leaving group (OSO₂F)]: 10.1%, fluoride: <5%) and a E:Z isomer ratio of 40:60 at the time of determination of the reaction conversion rate. The reaction terminated liquid was diluted with 30 mL of ethyl acetate, washed with 30 mL of an aqueous saturated potassium carbonate solution, further washed with 30 mL of water, and then, dried with anhydrous magnesium sulfate. The recovered organic phase was subjected to concentration under reduced pressure and purified by short column chromatography (silica gel, ethyl acetate-n-hexane system). With this, 0.63 g of α-trifluoromethyl-α,β-unsaturated ester of the following formula:

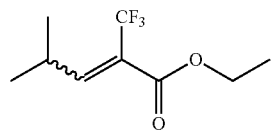

[Chem. 11]

was obtained as the purified product. It was confirmed that the yield of the product was 68%; the gas chromatographic purity of the product was 74.7%; and the E:Z isomer ratio of the product was 34:66. The ¹H-NMR and ¹⁹F-NMR data of the product are indicated below.

¹H-NMR [reference material: (CH₃)₄Si, deuterium solvent: CDCl₃] δ ppm; E isomer/1.05-1.15 (d, 6H), 1.25-1.40 (t, 3H), 3.29 (m, 1H), 4.20-4.35 (q, 2H), 6.56 (d, 10.2 Hz, 1H); Z isomer/1.05-1.15 (d, 6H), 1.25-1.40 (t, 3H), 3.08 (m, 1H), 4.20-4.35 (q, 2H), 6.97 (d, 11.0 Hz, 1H).

¹⁹F-NMR [reference material: C₆F₆, deuterium solvent: CDCl₃] δ ppm; E isomer/97.80 (s, 3F); Z isomer/103.05 (s, 3F).

Example 3

Into a pressure-proof reaction vessel of stainless steel (SUS) were placed 1.00 g (4.38 mmol, 1.00 eq) of α-trifluoromethyl-α-hydroxy ester of the following formula:

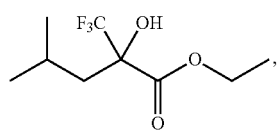

[Chem. 12]

5.0 mL (0.88 M) of acetonitrile and 1.97 g (12.94 mmol, 2.95 eq) of 1,8-diazabicyclo[5.4.0]undec-7-ene (DBU). The reaction vessel was immersed in a cooling bath of −78° C., followed by blowing 0.90 g (8.82 mmol, 2.01 eq) of sulfuryl fluoride (SO₂F₂) from a cylinder into the reaction vessel. The resulting liquid was stirred for one night at 50° C.

It was determined by gas chromatography of the reaction terminated liquid that the conversion rate of the reaction was 100%. It was also confirmed that the reaction product had a gas chromatographic purity of 96.9% (as corrected by subtracting the peak of the DBU) (intermediate [LG; leaving group (OSO₂F)]: 1.2%, fluoride: <5%) and an E:Z isomer ratio of 37:63 at the time of determination of the reaction conversion rate. The reaction terminated liquid was diluted with 30 mL of ethyl acetate, washed with 30 mL of an aqueous saturated potassium carbonate solution, further washed with 30 mL of water, and then, dried with anhydrous magnesium sulfate. The recovered organic phase was subjected to concentration under reduced pressure and purified by short column chromatography (silica gel, ethyl acetate-n-hexane system). With this, 0.74 g of α-trifluoromethyl-α,β-unsaturated ester of the following formula:

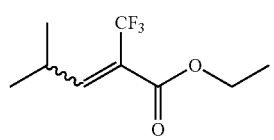

[Chem. 13]

was obtained as the purified product. It was confirmed that the yield of the product was 80%; the gas chromatographic purity of the product was 98.4%; and the E:Z isomer ratio of the product was 42:58. The ¹H-NMR and ¹⁹F-NMR data of the product were equivalent to those of Example 2.

Example 4

Into a pressure-proof reaction vessel of stainless steel (SUS) were placed 2.00 g (7.63 mmol, 1.00 eq) of α-trifluoromethyl-α-hydroxy ester of the following formula:

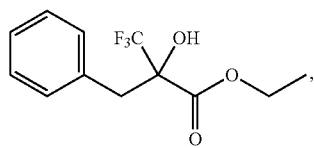

[Chem. 14]

10.0 mL (0.76 M) of acetonitrile and 3.48 g (22.86 mmol, 3.00 eq) of 1,8-diazabicyclo[5.4.0]undec-7-ene (DBU). The reaction vessel was immersed in a cooling bath of −78° C., followed by blowing 1.56 g (15.29 mmol, 2.00 eq) of sulfuryl fluoride (SO₂F₂) from a cylinder into the reaction vessel. The resulting liquid was stirred for one night at 50° C.

It was determined by gas chromatography of the reaction terminated liquid that the conversion rate of the reaction was 95%. It was also confirmed that the reaction product had a gas chromatographic purity of 90.6% (as corrected by subtracting the peaks of the DBU and substrate-derived impurities) (fluoride: <5%) and an E:Z isomer ratio of 90:10 at the time of determination of the reaction conversion rate. The reaction terminated liquid was diluted with 30 mL of ethyl acetate, washed with 30 mL of an aqueous saturated potassium carbonate solution, further washed with 30 mL of water, and then, dried with anhydrous magnesium sulfate. The recovered organic phase was subjected to concentration under reduced pressure and purified by short column chromatography (silica gel, ethyl acetate-n-hexane system). With this, 1.69 g of α-trifluoromethyl-α,β-unsaturated ester of the following formula:

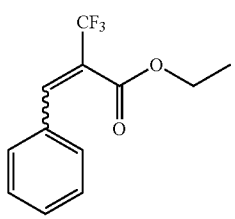

was obtained as the purified product. It was confirmed that the yield of the product was 91%; the gas chromatographic purity of the product was 90.5% (as corrected by subtracting the peaks of the substrate-derived impurities); and the E:Z isomer ratio of the product was 87:13. The $^1$H-NMR and $^{19}$F-NMR data of the product are indicated below.

$^1$H-NMR [reference material: $(CH_3)_4Si$, deuterium solvent: $CDCl_3$] δ ppm; E isomer/1.20 (t, 7.2 Hz, 3H), 4.26 (q, 7.2 Hz, 2H), 7.15-7.45 (Ar—H, 5H+s, 1H); Z isomer/1.15-1.45 (t, 3H), 4.05-4.45 (q, 2H), 7.15-7.45 (Ar—H, 5H), 8.09 (s, 1H).

$^{19}$F-NMR [reference material: $C_6F_6$, deuterium solvent: $CDCl_3$] δ ppm; E isomer/97.85 (s, 3F); Z isomer/103.81 (s, 3F).

Example 5

Into a pressure-proof reaction vessel of stainless steel (SUS) were placed 1.00 g (3.81 mmol, 1.00 eq) of α-trifluoromethyl-α-hydroxy ester of the following formula:

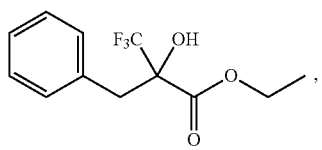

5.0 mL (0.76 M) of acetonitrile, 0.29 g (1.90 mmol, 0.50 eq) of 1,8-diazabicyclo[5.4.0]undec-7-ene (DBU) and 0.77 g (7.61 mmol, 2.00 eq) of triethylamine. The reaction vessel was immersed in a cooling bath of −78° C., followed by blowing 0.78 g (7.64 mmol, 2.01 eq) of sulfuryl fluoride ($SO_2F_2$) from a cylinder into the reaction vessel. The resulting liquid was stirred for one night at 50° C.

It was determined by gas chromatography of the reaction terminated liquid that the conversion rate of the reaction was 95%. It was also confirmed that the reaction product had a gas chromatographic purity of 80.2% (as corrected by subtracting the peaks of the DBU and substrate-derived impurities) (fluoride: <5%) and an E:Z isomer ratio of 90:10 at the time of determination of the reaction conversion rate. The reaction terminated liquid was diluted with 20 mL of ethyl acetate, washed with 20 mL of an aqueous saturated potassium carbonate solution, further washed with 20 mL of water, and then, dried with anhydrous sodium sulfate. The recovered organic phase was subjected to concentration under reduced pressure and then to vacuum drying. With this, 0.92 g of α-trifluoromethyl-α,β-unsaturated ester of the following formula:

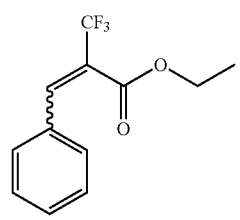

was obtained as the crude product. It was confirmed that the yield of the product was 99%; the gas chromatographic purity of the product was 83.6% (as corrected by subtracting the peaks of the substrate-derived impurities); and the E:Z isomer ratio of the product was 75:25. The $^1$H-NMR and $^{19}$F-NMR data of the product were equivalent to those of Example 4.

Example 6

Into a pressure-proof reaction vessel of stainless steel (SUS) were placed 3.00 g (13.26 mmol, 1.00 eq) of α-trifluoromethyl-α-hydroxy ester of the following formula:

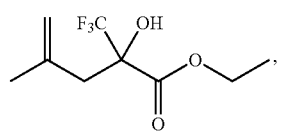

10.0 mL (1.33 M) of acetonitrile, 1.00 g (6.57 mmol, 0.50 eq) of 1,8-diazabicyclo[5.4.0]undec-7-ene (DBU) and 2.68 g (26.48 mmol, 2.00 eq) of triethylamine. The reaction vessel was immersed in a cooling bath of −78° C., followed by blowing 4.06 g (39.78 mmol, 3.00 eq) of sulfuryl fluoride ($SO_2F_2$) from a cylinder into the reaction vessel. The resulting liquid was stirred for one night at 50° C.

It was determined by gas chromatography of the reaction terminated liquid that the conversion rate of the reaction was 100%. It was also confirmed that the reaction product had a gas chromatographic purity of 96.1% (fluoride: <5%) and an E:Z isomer ratio of 92:8 at the time of determination of the reaction conversion rate. The reaction terminated liquid was diluted with 30 mL of ethyl acetate, washed with 30 mL of an aqueous saturated potassium carbonate solution, further washed twice with 30 mL of water, and then, dried with anhydrous magnesium sulfate. The recovered organic phase was subjected to concentration under reduced pressure and then to vacuum drying.

With this, 2.62 g of α-trifluoromethyl-α,β-unsaturated ester of the following formula:

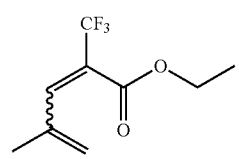

was obtained as the crude product. It was confirmed that the yield of the product was 95%; the gas chromatographic purity of the product was 97.9%; and the E:Z isomer ratio of the product was 92:8. The $^1$H-NMR and $^{19}$F-NMR data of the product are indicated below.

$^1$H-NMR [reference material: (CH$_3$)$_4$Si, deuterium solvent: CDCl$_3$] δ ppm; E isomer/1.33 (t, 7.2 Hz, 3H), 1.90 (s, 3H), 4.30 (q, 7.2 Hz, 2H), 5.31 (s, 1H), 5.33 (s, 1H), 6.83 (s, 1H); Z isomer/1.33 (t, 7.2 Hz, 3H), 1.93 (s, 3H), 4.30 (q, 7.2 Hz, 2H), 5.11 (s, 1H), 5.21 (s, 1H), 7.50 (s, 1H).

$^{19}$F-NMR [reference material: C$_6$F$_6$, deuterium solvent: CDCl$_3$] δ ppm; E isomer/98.05 (s, 3F); Z isomer/103.85 (s, 3F).

Example 7

Into a pressure-proof reaction vessel of stainless steel (SUS) were placed 50.00 g (249.80 mmol, 1.00 eq) of α-trifluoromethyl-α-hydroxy ester of the following formula:

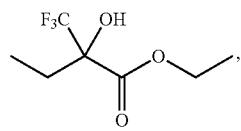

[Chem. 20]

83.0 mL (3.01 M) of acetonitrile, 19.00 g (124.80 mmol, 0.50 eq) of 1,8-diazabicyclo[5.4.0]undec-7-ene (DBU) and 63.20 g (624.57 mmol, 2.50 eq) of triethylamine. The reaction vessel was immersed in a cooling bath of −78° C., followed by blowing 51.00 g (499.71 mmol, 2.00 eq) of sulfuryl fluoride (SO$_2$F$_2$) from a cylinder into the reaction vessel. The resulting liquid was stirred for one night at room temperature.

It was determined by gas chromatography of the reaction terminated liquid that the conversion rate of the reaction was 99%. It was also confirmed that the reaction product had a gas chromatographic purity of 82.1% (fluoride: 9.0%) and an E:Z isomer ratio of 78:22 at the time of determination of the reaction conversion rate. The reaction terminated liquid was directly subjected to evaporation under reduced pressure (boiling point: 52 to 58° C., vacuum degree: 5000 Pa). With this, 17.21 g of α-trifluoromethyl-α,β-unsaturated ester of the following formula:

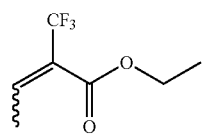

[Chem.21]

was obtained as the crude product. It was confirmed that the yield of the product was 38%; the gas chromatographic purity of the product was 82.8% (fluoride: 10.5%); and the E:Z isomer ratio of the product was 79:21. The $^1$H-NMR and $^{19}$F-NMR data of the product are indicated below.

$^1$H-NMR [reference material: (CH$_3$)$_4$Si, deuterium solvent: CDCl$_3$] δ ppm; E isomer/1.34 (t, 7.2 Hz, 3H), 2.17 (dq, 7.3 Hz, 2.2 Hz, 3H), 4.31 (q, 7.2 Hz, 2H), 6.95 (q, 7.3 Hz, 1H); Z isomer/1.25-1.40 (t, 3H), 2.09 (dq, 7.6 Hz, 2.8 Hz, 3H), 4.20-4.45 (q, 2H), 7.33 (q, 7.6 Hz, 1H).

$^{19}$F-NMR [reference material: C$_6$F$_6$, deuterium solvent: CDCl$_3$] δ ppm; E isomer/97.64 (s, 3F); Z isomer/103.00 (s, 3F).

Further, the $^1$H-NMR and $^{19}$F-NMR data of the fluoride of the following formula:

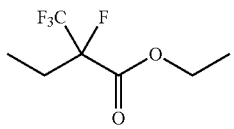

[Chem. 22]

are indicated below.

$^1$H-NMR [reference material: (CH$_3$)$_4$Si, deuterium solvent: CDCl$_3$] δ ppm; 1.25-1.40 (t, 3H+m, 3H), 3.65-3.85 (m, 1H), 3.85-4.00 (m, 1H), 4.20-4.45 (q, 2H).

$^{19}$F-NMR [reference material: C$_6$F$_6$, deuterium solvent: CDCl$_3$] δ ppm; 30.08 (s, 1F), 80.39 (s, 3F).

Comparative Example 1

To a methylene chloride solution (usage amount: 5.0 mL, 0.26 M) containing 0.30 g (1.31 mmol, 1.00 eq) of α-trifluoromethyl-α-hydroxy ester of the following formula:

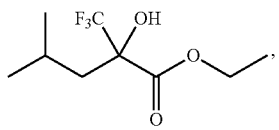

[Chem. 23]

0.58 g (2.06 mmol, 1.57 eq) of trifluoromethanesulfonic acid anhydride ((CF$_3$SO$_2$)$_2$O) was added under ice cooling. The resulting liquid was stirred for 10 minutes, followed by adding 0.26 g (3.29 mmol, 2.51 eq) of pyridine to the liquid while maintaining the liquid at the same temperature. The liquid was then further stirred for 1 hour. After that, the liquid was heated to room temperature and stirred for one night.

It was determined by gas chromatography of the reaction terminated liquid that the conversion rate of the reaction was 86%. It was also confirmed from the gas chromatography measurement for determination of the reaction conversion rate that α-trifluoromethyl-α,β-unsaturated ester of the following formula:

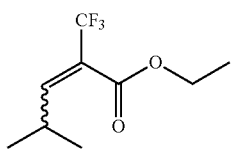

[Chem. 24]

was obtained with a gas chromatographic purity of 0.7% (intermediate (LG: leaving group (OSO$_2$CF$_3$)): 83.8%) and an E:Z isomer ratio of 60:40. No post treatment was performed on the reaction terminated liquid.

As shown in TABLE 1, Comparative Example 2 was carried out in the same manner as in Example 2 except for replacing the reactant. Similarly, Comparative Example 3 was carried out in the same manner as in Example 3 except for replacing the reactant as shown in TABLE 1. Further, Comparative Example 4 was carried out in the same manner as in Comparative Example 1 except for replacing the raw substrate (see reaction schemes of TABLES 1 and 2).

The invention claimed is:

1. A process for producing an α-trifluoromethyl-α,β-unsaturated ester of the general formula [2], comprising: reacting an α-trifluoromethyl-α-hydroxy ester of the general formula [1] with sulfuryl fluoride ($SO_2F_2$) in the presence of an organic base

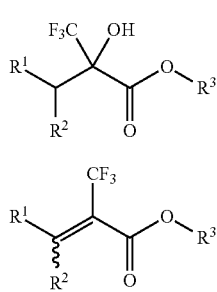

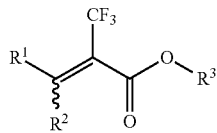

where $R^1$ and $R^2$ each independently represent a hydrogen atom, an alkyl group, a substituted alkyl group, an alkenyl group, a substituted alkenyl group, an alkynyl group, a substituted alkynyl group, an aromatic ring group, a substituted aromatic ring group, an alkylcarbonyl group, a substituted alkylcarbonyl group, an alkoxycarbonyl group, a substituted alkoxycarbonyl group, an arylcarbonyl group, a substituted arylcarbonyl group, a cyano group or a nitro group; $R^3$ represents an alkyl group or a substituted alkyl group; and the wavy line in the general formula (2) indicates that the double bond is in an E-isomer configuration, a Z-isomer configuration or a mixture thereof.

2. The process for producing the α-trifluoromethyl-α,β-unsaturated ester according to claim 1, wherein the α-trifluoromethyl-α,β-unsaturated ester is an α-trifluoromethyl-α,β-unsaturated ester of the general formula [4]; and wherein the α-trifluoromethyl-α-hydroxy ester is an α-trifluoromethyl-α-hydroxy ester of the general formula [3]

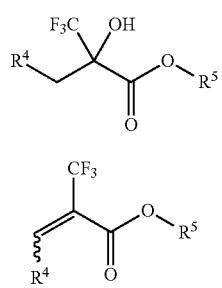

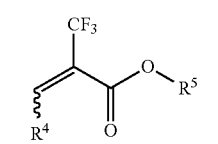

where $R^4$ represents an alkyl group, a substituted alkyl group, an alkenyl group, a substituted alkenyl group, an aromatic ring group or a substituted aromatic ring group; $R^5$ represents an alkyl group; the wavy line in the general formula [4] indicates that the double bond is in an E-isomer configuration, a Z-isomer configuration or a mixture thereof.

3. The process for producing the α-trifluoromethyl-α,β-unsaturated ester according to claim 1, wherein the organic base is either 1,5-diazabicyclo[4.3.0]non-5-ene (DBN) or 1,8-diazabicyclo[5.4.0]undec-7-ene (DBU).

* * * * *